(12) United States Patent
He et al.

(10) Patent No.: US 9,199,978 B2
(45) Date of Patent: Dec. 1, 2015

(54) ACRYLAMIDE COMPOUNDS AND USE THEREOF FOR INHIBITING APOPTOSIS

(75) Inventors: Kunluu He, Beijing (CN); Song Li, Beijing (CN); Wu Zhong, Beijing (CN); Juan Liu, Beijing (CN); Lili Wang, Beijing (CN); Xin Li, Beijing (CN); Guoliang Hu, Beijing (CN); Jie Wang, Beijing (CN); Long Long, Beijing (CN); Junhai Xiao, Beijing (CN); Zhibing Zheng, Beijing (CN); Wei Li, Beijing (CN); Ruijun Li, Beijing (CN); Chunlei Liu, Beijing (CN); Jie Tang, Beijing (CN)

(73) Assignee: CHINESE PLA GENERAL HOSPITAL, Beijing (CN)

( * ) Notice: Subject to any disclaimer, the term of this patent is extended or adjusted under 35 U.S.C. 154(b) by 303 days.

(21) Appl. No.: 13/697,810

(22) PCT Filed: May 14, 2010

(86) PCT No.: PCT/CN2010/000687
§ 371 (c)(1),
(2), (4) Date: Jan. 29, 2013

(87) PCT Pub. No.: WO2011/140681
PCT Pub. Date: Nov. 17, 2011

(65) Prior Publication Data
US 2013/0158022 A1    Jun. 20, 2013

(51) Int. Cl.
| | | |
|---|---|---|
| *A61K 31/5377* | (2006.01) | |
| *C07D 295/194* | (2006.01) | |
| *C07D 295/21* | (2006.01) | |
| *C07D 409/12* | (2006.01) | |
| *A61K 31/17* | (2006.01) | |
| *A61K 31/381* | (2006.01) | |
| *A61K 31/435* | (2006.01) | |
| *A61K 31/4709* | (2006.01) | |
| *A61K 31/496* | (2006.01) | |
| *C07C 335/12* | (2006.01) | |
| *C07D 333/24* | (2006.01) | |

(52) U.S. Cl.
CPC .............. *C07D 409/12* (2013.01); *A61K 31/17* (2013.01); *A61K 31/381* (2013.01); *A61K 31/435* (2013.01); *A61K 31/4709* (2013.01); *A61K 31/496* (2013.01); *A61K 31/5377* (2013.01); *C07C 335/12* (2013.01); *C07D 295/194* (2013.01); *C07D 295/21* (2013.01); *C07D 333/24* (2013.01)

(58) Field of Classification Search
CPC ............ C07D 333/24; C07D 295/194; C07D 295/21; C07D 409/12; A61K 31/17; A61K 31/435; A61K 31/496; A61K 31/5377; A61K 31/381; A61K 31/4709
See application file for complete search history.

(56) References Cited

U.S. PATENT DOCUMENTS

2002/0156285 A1 * 10/2002 Kunz et al. .................. 546/281.7

FOREIGN PATENT DOCUMENTS

| WO | WO 02/22581 A1 | 3/2002 |
| WO | WO 2007/101710 A1 | 9/2007 |
| WO | WO 2010/011898 A1 | 1/2010 |

OTHER PUBLICATIONS

International Search Report for Application No. PCT/CN2010/000687 dated Jan. 29, 2011, 9 pages.
B.Q. Kreider et al., "Enrichment of Schwann Cell Cultures From Neonatal Rat Sciatic Nerve by Differential Adhesion" Brain Research, 207 (1981) 433-444.
Kai Long et al., "Structure-Activity Relationship Studies of Salubrinal Lead to Its Active Biotinylated Derivative" Bioorganic & Medical Chemistry Letters 15 (2005) 3849-3852.
European Search Report for Application EP 10 85 1188 dated Oct. 8, 2013, 2 pages.
Extended European Search Report for Application EP 10 85 1188 dated Oct. 17, 2013, 7 pages.
European Office Action dated Jul. 2, 2014; 5 pages.

* cited by examiner

*Primary Examiner* — Rebecca Anderson
(74) *Attorney, Agent, or Firm* — Howard & Howard Attorneys PLLC

(57) ABSTRACT

The present invention relates to a compound of Formula I, or an isomer, pharmaceutically acceptable salt and solvate of the compound, and to a composition comprising the compound of Formula I, or the isomer, pharmaceutically acceptable salt and solvate thereof, and a pharmaceutically acceptable carrier, excipient or diluents. The present invention also relates to use of the compound of Formula I, or the isomer, pharmaceutically acceptable salt and solvate thereof for combating apoptosis, preventing or treating a disease or disorder associated with apoptosis; and especially use for protecting cardiomyocyte, and for preventing or treating a disease or disorder associated with cardiomyocyte apoptosis.

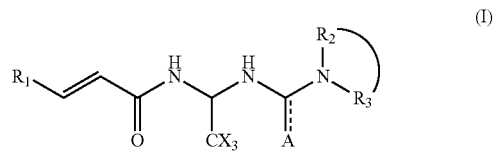

(I)

9 Claims, No Drawings

ACRYLAMIDE COMPOUNDS AND USE THEREOF FOR INHIBITING APOPTOSIS

RELATED APPLICATIONS

This application is the National Stage of International Patent Application No. PCT/CN2010/000687, filed on May 14, 2010, the content of which is incorporated herein by reference.

FIELD OF THE INVENTION

The present invention relates to the field of medical chemistry. Specifically, the present invention relates to an acrylamide compound and a pharmaceutical composition thereof. The present invention further relates to use of a urea compound and a pharmaceutical composition thereof for anti-apoptosis, prophylaxis or treatment of a disease or disorder associated with apoptosis, especially for protecting myocardial cells and for prophylaxis or treatment of a disease or disorder associated with apoptosis of myocardial cells.

BACKGROUND OF THE INVENTION

Apoptosis usually refers to programmed cell death of body cells occurred via the regulation of intracellular genes and products thereof during development process or under the action of some factors. Apoptosis commonly exists in biosphere under both physiological state and pathological state. It plays important roles in embryo development and morphogenesis, stability of normal cells in tissues, defense and immune reaction of body, cell damage caused by diseases or poisoning, ageing, generation and development of tumors, and is one of the hottest spots in biomedical research.

Some researches show that the occurrence of many serious diseases relates to the over apoptosis of cells, for example, the reduction of CD4$^+$ T cells during the development of ADIS; the cell death mediated by cytotoxic T cell during transplant rejection reaction; the apoptosis of myocardial cells and nerve cells of ischemia and reperfusion injury; nervous system degradation diseases (such as Alzheimer disease, Parkinson's disease, etc.); apoptosis caused by exposure to ionizing radiation in many tissues.

Some evidences have indicated that cardiomyocytes apoptosis closely associates with the occurrence, development and prognosis of many heart diseases. It is found in the research about cardiomyocytes apoptosis that the infarct of cardiac muscle is not equivalent to myocardial necrosis, and apoptosis is one of mechanisms of myocardial infarction, and is the main manner of myocardial death of early infarction and myocardial death caused by ischemia/reperfusion, and the apoptosis of cardiomyocytes in large amount at this time aggravates myocardial damage. In 1989, Nepomniashchikh et al found in the observation of ultrastructure of hunger myocardial atrophy that the synthesis of cardiomyocytes structural protein decreased, and the cell number decreased but was not accompanied with a proportional decrease of cell nucleus, an thus preliminarily proposed that hunger myocardial atrophy was caused by apoptosis. In 1994, Gottlieb and Kawano et al obtained direct evidences of cardiomyocytes apoptosis by using electron microscope in combination with DNA gel electrophoresis, in which the former disclosed reperfusion injury induced rabbit cardiomyocytes apoptosis, and the latter confirmed that myocarditis patients had concomitant cardiomyocytes apoptosis. Tanaka et al also confirmed the existence of apoptosis of cardiomyocytes in suckling mice. With the progress of methodology and research of apoptosis, pathological functions of cardiomyocytes apoptosis have been found in many heart diseases. Some researches indicate the heart injury in spontaneously hypertensive rat (SHR) is relevant to apoptosis; the conversion from cardiac pachynsis to heart failure in advanced stage is caused by cardiomyocytes apoptosis; acute myocardial infarction also induces apoptosis in early stage of infarction and reperfusion injury, except necrosis; cardiomyocytes apoptosis is also found in transplanted heart and right ventricular maldevelopment myocardial diseases, and anoxia also induces cardiomyocytes apoptosis.

Apoptosis has recoverability in some extents, and the apoptosis in myocardial infarction and ischemia/reperfusion has its own features and regular patterns, so that the features may be used for prevention and reduction of apoptosis and may provide enlightenments for clinical prophylaxis of ischemia/reperfusion injury; during the process of reperfusion, the apoptosis occurred in contraction band region (around infarction site) is induced by some precipitating factors, so that the inhibition factors of apoptosis such as drugs may be used for preventing apoptosis and treating corresponding diseases caused by apoptosis.

However, there are few kinds and numbers of drugs so far that can be clinically used for anti-apoptosis and protecting cells, and their selectivity and targeting property are not satisfied, and therefore it is of great significance to continuously develop new, safe and effective drugs for anti-apoptosis and protecting cells, and especially drugs with a novel mechanism of action.

SUMMARY OF THE INVENTION

In order to develop a novel, safe and effective drug for anti-apoptosis and protecting cells, the present inventors find for a long time and by massive experimental researches that a kind of acrylamide compound that has functions for anti-apoptosis and protecting myocardial cells, and can be useful for prophylaxis or treatment of diseases or disorders associated with cardiomyocyte apoptosis. Specifically, The first aspect of the present invention relates to a compound of Formula I, or an isomer, pharmaceutically acceptable salt or solvate thereof.

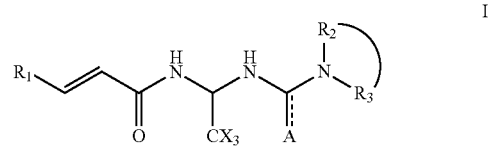

wherein

A represents =S or —SR$_4$;

X represents F, Cl, Br or I;

R$_1$ represents thienyl or substituted thienyl, wherein said thienyl, thiazolyl is unsubstituted or substituted with 1-3 (e.g., 1-2, 1, 2, or 3) substituents selected from: halogens, nitro, hydroxyl, amino, cyano, C1-C6 alkyl, C1-C6 alkoxy, and C1-C6 halogenated alkyl, and wherein said alkyl, alkoxy and halogenated alkyl can be optionally substituted with hydroxy, —O—(C1-C4)-alkyl, oxo, amino, —NH—(C1-C4)-alkyl, or —N—[(C1-C6)-alkyl]$_2$, or said alkyl, alkoxy and halogenated alkyl can be optionally substituted with —O—, —S—, —NH—, —COO—;

R$_2$, R$_3$ represent hydrogen, C1-C6 alkyl, C3-C6 cycloalkyl, substituted C3-C6 cycloalkyl, C1-C6 alkoxy C1-C6 alkyl, amino C1-C6 alkyl, mono-substituted or disubstituted amino C1-C6 alkyl, phenyl C1-C6 alkyl, substituted phenyl C1-C6 alkyl, heterocyclic group C1-C6 alkyl, phenyl, substituted phenyl, heterocyclic group or substituted heterocyclic group, wherein $R_2$ and $R_3$ may be attached together to form a saturated cyclic alkyl, nitrogen- or oxygen-containing heterocyclic group;

$R_4$ represents C1-C6 alkyl.

Preferably selected is a compound of Formula (I), or an isomer, pharmaceutically acceptable salt and solvate thereof, wherein:

A represents =S or —$SR_4$;

$R_1$ represents thienyl or substituted thienyl;

$R_2$, $R_3$ represent hydrogen, C1-C6 alkyl, C3-C6 cycloalkyl, substituted C3-C6 cycloalkyl, C1-C6 alkoxy C1-C6 alkyl, amino C1-C6 alkyl, mono-substituted or di-substituted amino C1-C6 alkyl, phenyl C1-C6 alkyl, substituted phenyl C1-C6 alkyl, heterocyclic group C1-C6 alkyl, phenyl, substituted phenyl, heterocyclic group or substituted heterocyclic group, wherein $R_2$ and $R_3$ may be attached together to form a saturated cyclic alkyl, nitrogen- or oxygen-containing heterocyclic group;

$R_4$ represents methyl, ethyl, propyl, isopropyl, butyl, pentyl.

In particular, the preferably selected is a compound of Formula (I), or an isomer, pharmaceutically acceptable salt and solvate, wherein:

A represents =S or —$SR_4$;

$R_1$ represents 2-thienyl or 3-thienyl;

$R_2$, $R_3$ represents hydrogen, methyl, isopropyl, 2-methoxyethyl, 3-isopropoxypropyl, 2-N,N-dimethyl ethyl, cyclohexyl, cycloheptyl, o-methoxyphenyl, o-fluorophenyl, o-chlorophenyl, p-chlorophenyl, benzyl or 8-quinolyl, wherein $R_2$ and $R_3$ may be attached together to form a piperidine ring, morpholine ring or N-methyl piperazine ring;

$R_4$ represents methyl.

The compound of Formula (I), or an isomer, pharmaceutically acceptable salt and solvate thereof, is particularly selected from the following compounds:

(1) (2E)-3-(2-thienyl)-N-[1-(8-quinolylamino)thioformylamino-2,2,2-trichloroethyl]-2-acrylamide;

(2) (2E)-3-(3-thienyl)-N-[1-(8-quinolylamino)thioformylamino-2,2,2-trichloroethyl]-2-acrylamide;

(3) (2E)-3-(2-thienyl)-N-[1-(4-tolylamino)thioformylamino-2,2,2-trichloroethyl]-2-acrylamide;

(4) (2E)-3-(2-thienyl)-N-[1-(2-methoxyanilino)thioformylamino-2,2,2-trichloroethyl]-2-acrylamide;

(5) (2E)-3-(2-thienyl)-N-(1-benzylaminothioformylamino-2,2,2-trichloroethyl)-2-acrylamide;

(6) (2E)-3-(2-thienyl)-N-(1-cyclohexylaminothioformylamino-2,2,2-trichloroethyl)-2-acrylamide;

(7) (2E)-3-(2-thienyl)-N-[1-isopropylaminothioformylamino-2,2,2-trichloroethyl]-2-acrylamide;

(8) (2E)-3-(2-thienyl)-N-[1-(2-fluoroanilino)thioformylamino-2,2,2-trichloroethyl]-2-acrylamide;

(9) (2E)-3-(2-thienyl)-N-[1-(3-isopropoxypropylamino) thioformyl amino-2,2,2-trichloroethyl]-2-acrylamide;

(10) (2E)-3-(2-thienyl)-N-[1-(2-methoxyformylanilino) thioformyl amino-2,2,2-trichloroethyl]-2-acrylamide;

(11) (2E)-3-(2-thienyl)-N-(1-cycloheptylaminothioformylamino-2,2,2-trichloroethyl)-2-acrylamide;

(12) (2E)-3-(2-thienyl)-N-[1-(1-morpholinyl)thioformylamino-2,2,2-trichloroethyl]-2-acrylamide;

(13) (2E)-3-(2-thienyl)-N-[1-(4-methylpiperazinyl)thioformyl amino-2,2,2-trichloroethyl]-2-acrylamide;

(14) (2E)-3-(2-thienyl)-N-[1-(8-quinolylamino)methylthio methenylamino-2,2,2-trichloroethyl]-2-acrylamide;

(15) (2E)-3-phenyl-[1-(1-morpholinyl)thioformylamino-2,2,2-trichloroethyl]-2-acrylamide;

(16) (2E)-3-phenyl-[1-(1-piperidyl)thioformylamino-2,2,2-trichloroethyl]-2-acrylamide;

(17) (2E)-3-phenyl-[1-(3-methoxy benzyl)thioformylamino-2,2,2-trichloroethyl]-2-acrylamide.

The compound of Formula (I) of the present invention can be prepared by the following method:

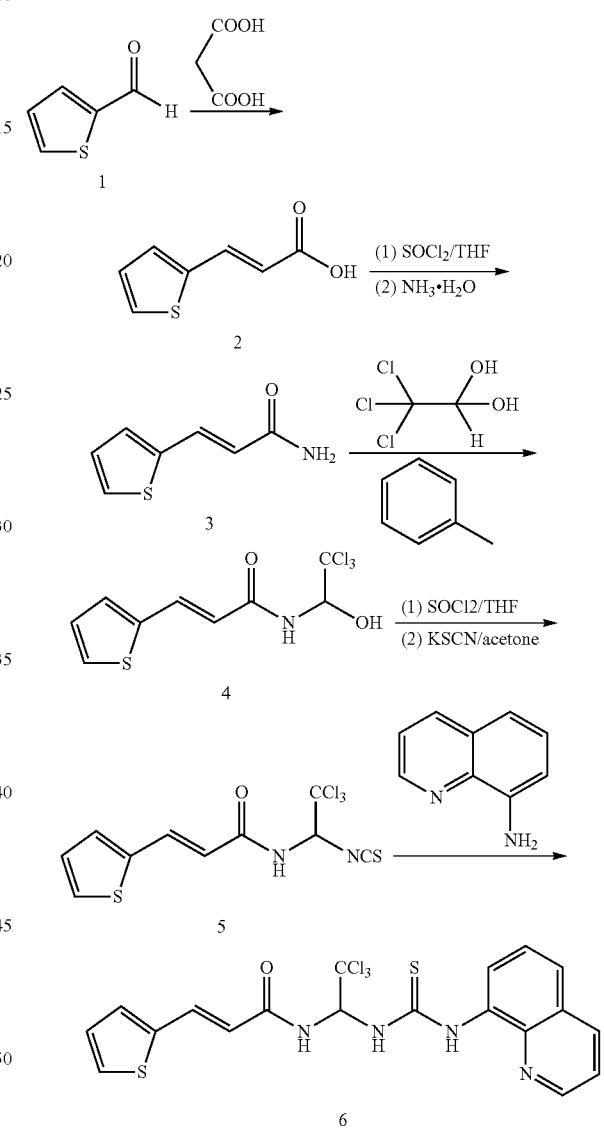

By taking Compound 6 as example, the compound of the present invention is synthesized by using 2-thiophene carboxaldehyde as initial raw material, acting with malonic acid in pyridine as solvent in the presence of piperidine as catalyst to generate Compound 2, then reacting with thionyl chloride to prepare an acyl chloride, a concentrated ammonia water dropwise added to obtain Compound 3, refluxing 3 with trichloroacetaldehyde hydrate in toluene to obtain Compound 4, then chloridizing and reacting with potassium thiocyanate to obtain isothiocyanate 5, finally refluxing with 8-aminoquinoline to obtain Compound 6.

Another aspect of the present invention relates to a pharmaceutical composition, comprising a compound of Formula (I), or an isomer, salt and solvate thereof, a pharmaceutically acceptable carrier, excipient or a diluent.

The present invention further relates to use of the compound of Formula (I) or an isomer, pharmaceutically acceptable salt and solvate thereof according to the first aspect of the present invention for the manufacture of a medicament for anti-apoptosis, or preventing or treating a disease or disorder associated with apoptosis.

The present invention further relates to a use of the compound of Formula (I) or an isomer, pharmaceutically acceptable salt and solvate thereof according to the first aspect of the present invention for the manufacture of a medicament for protecting cardiomyocytes and preventing or treating a disease or disorder associated with cardiomyocyte apoptosis.

The present invention further relates to a method for anti-apoptosis, or preventing or treating a disease or disorder associated with apoptosis, the method comprising administering a subject in need thereof a therapeutically effective amount of a compound of Formula (I) or an isomer, pharmaceutically acceptable salt and solvate thereof according to the first aspect of the present invention.

The present invention further relates to a method for protecting cardiomyocyte, or preventing or treating a disease or disorder associated with cardiomyocyte apoptosis, the method comprising administering a subject in need thereof a therapeutically effective amount of a compound of Formula (I) or an isomer, pharmaceutically acceptable salt and solvate thereof.

The disease or disorder associated with apoptosis according to the present invention comprises: cardiovascular diseases, nerve degenerative diseases, multiple sclerosis, viral infections, etc.

The disease or disorder associated with cardiomyocyte apoptosis according to the present invention includes but is not limited to: (i) hunger myocardial atrophy, (ii) myocarditis, (iii) heart failure, (iv) myocardial damage caused by primary hypertension, (v) myocardial damage caused by early stage of acute myocardial infarction, (vi) myocardial damage caused by acute myocardial infarction reperfusion, (vii) pathological changes of cardiomyocytes caused by heart transplantation, or (viii) displastic mycocardiosis; or cardiomyocytes apoptosis caused by anoxia, or sclerosis in cardiovascular system.

According to the present invention, the term "heterocyclic ring" includes but is not limited to: pyridine, pyrrole, furan, thiophene, pyrazole, imidazole, thiazole, oxazole, isoxazole, indole, benzofuran, benzimidazole, carbazole, pyridazine, pyrimidine, pyrazine, quinoline, isoquinoline, purine, phenothiazine, and phenazine.

Those skilled in the art would appreciate that the compound of Formula I has a chiral center. When a single enantiomer of the compound of Formula I is required, it can be prepared by using reactants present in single enantiomer form in all possible steps, or prepared by performing reaction in the presence of an reagent or catalyst in single enantiomer form, or prepared by resolution of a mixture of stereoisomers via conventional methods. Some preferable methods comprises resolution using microorganisms, resolution and chiral acid such as any usable acid for example mandelic acid, camphor sulfonic acid, tartaric acid, lactic acid, etc. form diastereomer salt, or resolution and chiral base such as bracine, cinchona alkaloid or derivatives thereof form diastereomer salt. The commonly used methods can be seen in "Enantiomers, Racemates and Resolution" as edited by Jaques et al (Wiley Interscience, 1981).

Those skilled in the art should appreciate that the compound of the present invention can also be used in form of its pharmaceutically acceptable salt or solvate. The physiologically acceptable salts of the compound of Formula I include conventional salts formed with pharmaceutically acceptable inorganic acid or organic acid or inorganic base or organic base and acid addition salt of quaternary ammonium. More specific examples of suitable acid salts include salts of hydrochloric acid, hydrobromic acid, sulfuric acid, phosphoric acid, nitric acid, perchloric acid, fumaric acid, acetic acid, propionic acid, succinic acid, hydroxyacetic acid, formic acid, lactic acid, maleic acid, tartaric acid, citric acid, pamoic acid, malonic acid, hydroxymaleic acid, phenylacetic acid, glutamic acid, benzoic acid, salicylic acid, fumaric acid, toluene sulfonic acid, methylsulfonic acid, naphthalene-2-sulfonic acid, benzene sulfonic acid, hydroxynaphthoic acid, hydroiodic acid, malic acid, steroic, tannic acid, etc. As for other acids, such as oxalic acid, although they per se are not pharmaceutically acceptable, they can be used for prepare salts as intermediates to obtain the compound of the present invention and pharmaceutically acceptable salts thereof. More specific suitable alkali salts include salts of sodium, lithium, potassium, magnesium, aluminum, calcium, zinc, N,N'-dibenzylethylenediamine, chloroprocaine, choline, diethanolamine, ethylenediamine, N-methylglucosamine, and procaine. The compounds of the present invention as mentioned thereafter include the compound of Formula I and a pharmaceutically acceptable salt and solvate thereof.

The present invention further comprises a prodrug of the compound of the present invention, and once the prodrug is administered, it is chemically converted via metabolic procedure into an active drug. In general, this kind of prodrug is a functional derivative of the compound of the present invention, which can be readily converted into the needed compound of Formula (I). For example, "Design Of Prodrugs", edited by H Bund Saard, Elsevier, 1985, describes conventional methods of selecting and preparing suitable prodrug derivatives.

The present invention also includes any active metabolites of the compound of the present invention.

Another aspect of the present invention relates to a pharmaceutical composition comprising a racemic or optical isomer of the compound of the present invention, and at least one pharmaceutically acceptable carrier, and being useful in in vivo treatment and having biocompatibility. The pharmaceutical composition can be processed into various forms for different administration routes. The compound of the present invention can also be processed into various pharmaceutically acceptable salts.

The pharmaceutical composition of the present invention comprises an effective amount of the compound of Formula I of the present invention or a pharmaceutically acceptable salt or hydrate thereof and one or more suitable pharmaceutically acceptable carriers. The pharmaceutically acceptable carriers comprise but are not limited to: ion exchangers, alumina, aluminum stearate, lecithin, serum protein such as human albumin, buffering substance such as phosphate, glycerol, sorbic acid, potassium sorbate, mixture of partial glycerides of saturated plant fatty acids, water, salts or electrolytes, such as protamine sulfate, disodium hydrogen phosphate, potassium hydrogen phosphate, sodium chloride, zinc salt, colloid silica, magnesium trisilicate, polyvinylpyrrolidone, cellulose substances, polyethylene glycol, sodium carboxymethylcellulose, polyacrylates, beeswax, and lanolin.

The pharmaceutical composition of the compound of the present invention can be administered by any of the following manners: oral administration, spray inhalation, rectal administration, nasal administration, bucca administration, local administration, parenteral administration, such as subcutaneous, intravenous, intramuscular, intraperitoneal, intrathecal, intraventricular, intrasternal, intracranial injection or perfusion, or administration with aid of an explanted reservoir, preferably oral administration, intraperitoneal or intravenous administration.

For oral administration, the compound of the present invention can be processed in any acceptable forms for oral administration, including but not being limited to tablets, capsules, water solutions or water suspensions. The tablets use a carrier generally comprising lactose and maize starch, additionally comprising a lubricant such as magnesium stearate. The capsules use a diluent generally comprising lactose and dry maize starch. The water suspensions usually use a mixture of an active component and suitable emulsifying agent and suspending agent. If necessary, the above oral dosage forms can further comprise some sweetening agents, flavoring agents or coloring agents.

For local administration, especially in treatment of neurogenic disease of a readily accessible affected surface or organ such as eye, skin or inferior part of intestinal tract by local external application, the compound of the present invention can be processed into different dosage forms for local administration according to different affected surfaces or organs, which are illustrated as follows:

For local administration to eyes, the compound of the present invention can be processed in a dosage form of micronized suspension or solution, in which the used carrier is isotonic sterile saline with a certain pH, wherein a preservative such as chlorobenzylalkanol salt can be added or not be added. For the eye use, the compound can be processed into ointment form, such as Vaseline ointment.

For local administration to skin, the compound of the present invention can be processed in suitable dosage forms such as ointments, lotions or creams, wherein the active component is suspended or dissolved in one or more carriers. The carriers usable in ointments include but are not limited to: mineral oil, liquid paraffin, white Vaseline, propylene glycol, polyethylene oxide, polypropylene oxide, emulsified wax and water; the carriers usable in lotions or creams comprise but are not limited to: mineral oil, sorbitan monostearate, Tween 60, hexadecane ester wax, hexadecylene aromatic alcohol, 2-octyldodecanol, benzyl alcohol and water.

The compound of the present invention can further be administered in dosage form of sterile injections, including water or oil suspensions for sterile injection, or sterile injection solutions. The usable carriers and solvents include water, Ringer's solution and isotonic sodium chloride solution. In addition, sterile nonvolatile oil can also be used as solvent or suspending medium, such as monoglyceride or diglyceride.

It should be further pointed out that the dose and usage method of the compound of the present invention depend on many factors, including age, body weight, gender, natural health status, nutritional status, activity of compound, administration time, metabolic rate, severity of disease and subjective judgment of diagnostic doctor.

BENEFICIAL EFFECTS OF THE INVENTION

The present invention provides a kind of acrylamide compounds, and demonstrates it has functions of anti-apoptosis and cells-protecting, and thus provides a new method and approach for treatment of diseases or disorders caused by apoptosis, especially for treatment of diseases or disorders caused by cardiomyocyte apoptosis.

EMBODIMENTS OF THE INVENTION

The embodiments of the present invention are illustrated as follows in combination with examples. However, those skilled in the art would understand that the following examples are merely to illustrate the present invention and should not be deemed as restriction of the present invention. The examples which specific conditions are not given are performed according to conventional conditions or conditions suggested by manufacturers. The reagents or instruments which manufacturers are not given are all conventional products commercially available from markets.

The melting points of compounds were measured by RY-1 melting point instrument, and thermometers were not calibrated. Mass spectrums were measured by Micromass Zab-Spec high resolution mass spectrometer (resolution: 1000). $^1$H NMR was measured by JNM-ECA-400 superconducting NMR meter, working frequency: $^1$H NMR 400 MHz, $^{13}$C NMR 100 MHz.

EXAMPLE 1

(2E)-3-(2-thienyl)-N-[1-(8-quinolylamino)thioformyl amino-2,2,2-trichloroethyl]-2-acrylamide

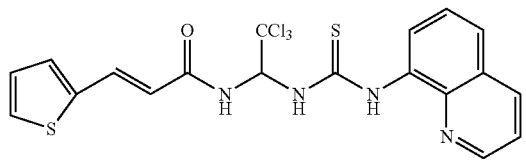

1.12 g of 2-thiophene carboxaldehyde and 3.12 g of malonic acid were dissolved in 15 ml of pyridine, added with a catalytically effective amount of piperidine, reacted at 80° C. for 6 h, the reaction solution was poured into 20 ml of water, regulated with 10% NaOH aqueous solution to reach PH 12, extracted with ethyl acetate, the water layer was taken and regulated with 2N hydrochloric acid to reach PH3, a large amount of yellow solid (2E)-3-(2-thienyl)acrylic acid was precipitated, filtered and washed with water to obtain 1.12 g. The (2E)-3-(2-thienyl)acrylic acid was dissolved in 10 ml of anhydrous dichloromethane, added with a catalytically amount of DMF, added dropwise with 1.5 ml of oxalyl chloride under ice-water bath, after adding dropwise, heated to room temperature, stirred for 2 h, the reaction solution was added dropwise into 0° C. 10 ml concentrated ammonia water, stirred for 30 min, the layers were separated, the dichloromethane layer was taken, evaporated to remove solvent and obtain white needle crystal (2E)-3-(2-thienyl)acrylamide 0.7 g. It together with 1.20 g of trichloroacetaldehyde hydrate was added to 30 ml of toluene, refluxed at 110° C. for 8 h, cooled to room temperature to precipitate a large amount of yellow lamellar crystal (2E)-3-(2-thienyl)-N-(1-hydroxy-2,2,2-trichloroethyl)acrylamide 1.20 g. It was dissolved in 20 ml anhydrous THF, added with DMF for catalysis, added dropwise with SOCl$_2$ 1.2 ml at room temperature, heated to 60° C. and reacted for 2 h. After solvent was evaporated, it was dissolved in anhydrous acetone, added with 0.3 g of KSCN, stirred and reacted at 40° C. for 2 h, filtered with diatomite, the filtrate was eluted with developing solvent system of petroleum ether:ethyl acetate=20:1, to obtain yellow needle crystal (2E)-3-(2-thienyl)-N-(1-isothiocyano-2,2,2-trichloroethyl)acrylamide 0.81 g. It was dissolved in 10 ml of THF, added with 0.30 g of 8-aminoquinoline, heated to 60° C. and reacted for 2 h, cooled to room temperature to precipitate a large amount of white flocculent solid (2E)-3-(2-thienyl)-N-[1-(8-quinolylamino)thioformylamino-2,2,2-trichloroethyl]-2-acrylamide, which was recrystallized with THF to obtain a pure product of 0.92 g. $^1$H-NMR (400 MHz, DMSO-d$_6$) δ6.63-6.67 (d, 1H); δ7.12-7.14 (q, 1H); δ7.42-7.43 (d, 1H); δ7.53-7.73 (m, 6H); δ8.42-8.44 (dd, 1H); δ8.95-9.03 (m, 3H); δ9.54-9.56 (d, 1H); δ11.03 (s, 1H). MS (TOF) 487.0 (M+).

EXAMPLE 2

(2E)-3-(3-thienyl)-N-[1-(8-quinolylamino)thioformyl amino-2,2,2-trichloroethyl]-2-acrylamide

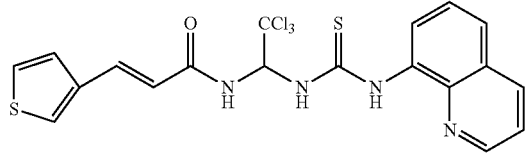

The method of Example 1 was used, in which 2-thiophene carboxaldehyde was replaced with 3-thiophene carboxaldehyde, to obtain yellow solid 0.60 g. $^1$H-NMR (400 MHz, DMSO-d$_6$) δ6.67-6.71 (d, 1H); δ7.35-7.36 (d, 1H); δ7.54-7.72 (m, 6H); δ7.87-7.88 (d, 1H); δ8.42-8.44 (dd, 1H); δ8.96-9.03 (m, 3H); δ9.54-9.56 (d, 1H); δ11.05 (s, 1H). MS (TOF) 487.0 (M+).

EXAMPLE 3

(2E)-3-(2-thienyl)-N-[1-(4-tolylamino)thioformyl amino-2,2,2-trichloroethyl]-2-acrylamide

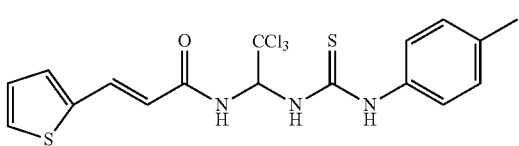

The method of Example 1 was used, in which 8-aminoquinoline was replaced with 4-methylaniline, to obtain yellow solid 60 mg. $^1$H-NMR (400 MHz, DMSO-d$_6$) δ2.28 (s, 3H); δ6.47-6.51 (d, 1H); δ7.13-7.18 (m, 3H); δ7.36-7.45 (m, 4H); δ7.66-7.72 (m, 2H); δ8.03 (, 1H); δ8.96-8.98 (d, 1H); δ10.21 (s, 1H). MS (TOF) 450.0 (M+).

EXAMPLE 4

(2E)-3-(2-thienyl)-N-[1-(2-methoxyanilino)thioformylamino-2,2,2-trichloroethyl]-2-acrylamide

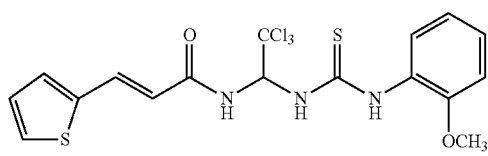

The method of Example 1 was used, in which 8-aminoquinoline was replaced with 2-methoxyaniline, to obtain yellow solid 0.23 g. $^1$H-NMR (400 MHz, DMSO-d$_6$) δ3.83 (s, 3H); δ6.52-6.56 (d, 1H); δ6.90-7.14 (m, 4H); δ7.41-7.45 (m, 2H); δ7.65-7.72 (m, 2H); δ7.90-7.92 (d, 1H); δ8.48 (s, 1H); δ9.00-9.02 (d, 1H); δ9.80 (s, 1H). MS (TOF) 464.0 (M+).

EXAMPLE 5

(2E)-3-(2-thienyl)-N-(1-benzylaminothioformyl amino-2,2,2-trichloroethyl)-2-acrylamide

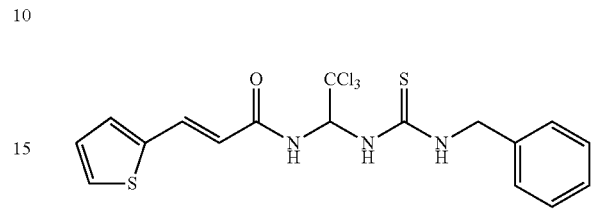

The method of Example 1 was used, in which 8-aminoquinoline was replaced with benzylamine, to obtain yellow solid 0.12 g. $^1$H-NMR (400 MHz, DMSO-d$_6$) δ4.68-4.69 (d, 2H); δ6.52-6.56 (d, 1H); δ6.52-6.56 (d, 1H); δ7.11-7.14 (dd, 1H); δ7.31-7.43 (m, 7H); δ7.64-7.71 (m, 2H); δ8.00-8.03 (d, 1H); δ8.61-8.63 (t, 1H); δ8.94-8.96 (d, 1H). MS (TOF) 447.9 (M+).

EXAMPLE 6

(2E)-3-(2-thienyl)-N-(1-cyclohexylaminothio formylamino-2,2,2-trichloroethyl)-2-acrylamide

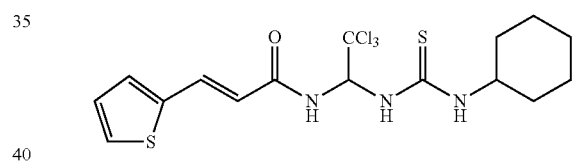

The method of Example 1 was used, in which 8-aminoquinoline was replaced with cyclohexylamine, to obtain yellow solid 0.22 g. $^1$H-NMR (400 MHz, DMSO-d$_6$) δ1.14-1.31 (m, 5H); δ1.51-1.64 (m, 3H); δ1.88 (m, 2H); δ3.97-3.99 (, 1H); δ6.51-6.55 (d, 1H); δ7.12-7.14 (dd, 1H); δ7.30-7.43 (m, 2H); δ7.65-7.83 (m, 3H); δ8.17-8.19 (d, 1H); δ8.91-8.93 (d, 1H). MS (TOF) 440.0 (M+).

EXAMPLE 7

(2E)-3-(2-thienyl)-N-[1-isopropylamino thioformylamino-2,2,2-trichloroethyl]-2-acrylamide

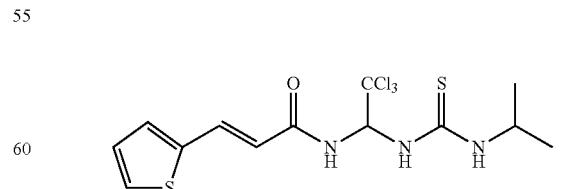

The method of Example 1 was used, in which 8-aminoquinoline was replaced with isopropylamine, to obtain yellow solid 0.29 g. $^1$H-NMR (400 MHz, DMSO-d$_6$) δ1.11-1.13 (m, 6H); δ4.21-4.24 (dd, 1H); δ6.51-6.55 (d, 1H); δ7.12-7.14 (dd, 1H); δ7.30-7.43 (m, 2H); δ7.65-7.76 (m, 3H); δ8.15-8.17 (d, 1H); δ8.91-8.93 (d, 1H). MS (TOF) 401.9 (M+).

EXAMPLE 8

(2E)-3-(2-thienyl)-N-[1-(2-fluoroanilino)thioformyl amino-2,2,2-trichloroethyl]-2-acrylamide

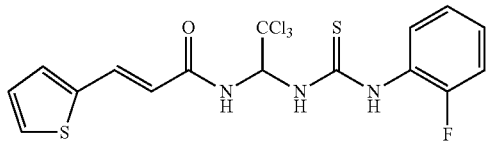

The method of Example 1 was used, in which 8-aminoquinoline was replaced with 2-fluoroaniline, to obtain yellow solid 0.30 g. $^1$H-NMR (400 MHz, DMSO-d$_6$) δ6.52-6.56 (d, 1H); δ7.12-7.29 (m, 4H); δ7.39-7.45 (m, 2H); δ7.66-7.73 (m, 2H); δ7.86-7.90 (t, 1H); δ8.52-8.54 (d, 1H); δ904-9.06 (d, 1H). MS (TOF) 453.0 (M+).

EXAMPLE 9

(2E)-3-(2-thienyl)-N-[1-(3-isopropoxypropylamino)thioformyl amino-2,2,2-trichloroethyl]-2-acrylamide

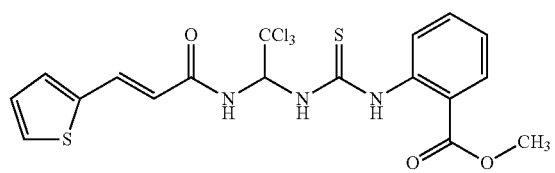

The method of Example 1 was used, in which 8-aminoquinoline was replaced with 3-isopropoxy n-propylamine, to obtain yellow solid 0.20 g. $^1$H-NMR (400 MHz, DMSO-d$_6$) δ1.06-1.08 (d, 6H); δ1.68-1.71 (t, 2H); δ3.31-3.51 (m, 4H); δ6.52-6.55 (d, 1H); δ7.11-7.13 (dd, 1H); δ7.31-7.43 (m, 2H); δ7.64-7.70 (m, 2H); δ7.86-7.88 (d, 1H); δ8.20-8.22 (t1H); δ8.88-8.90 (d, 1H). MS (TOF) 458.0 (M+).

EXAMPLE 10

(2E)-3-(2-thienyl)-N-[1-(2-methoxyformylanilino)thioformyl amino-2,2,2-trichloroethyl]-2-acrylamide

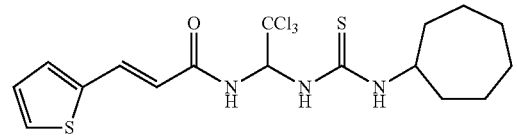

The method of Example 1 was used, in which 8-aminoquinoline was replaced with 2-methoxyformylaniline, to obtain purple white solid 0.36 g. $^1$H-NMR (400 MHz, DMSO-d$_6$) δ3.79-3.80 (s, 3H); δ6.59-6.62 (d, 1H); δ7.12-7.14 (dd, 1H); δ7.28-7.32 (m, 1H); δ7.42-7.46 (m, 2H); δ7.55-7.59 (m, 1H); δ7.65-7.72 (m, 2H); δ7.77-7.79 (d, 1H) δ7.84-7.86 (dd, 1H); δ8.88-9.01 (m, 2H). MS (TOF) 492.0 (M+).

EXAMPLE 11

(2E)-3-(2-thienyl)-N-(1-cycloheptylaminothioformyl amino-2,2,2-trichloroethyl)-2-acrylamide

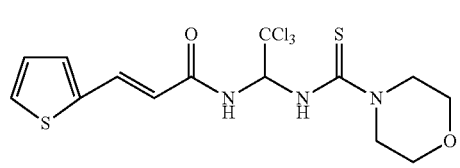

The method of Example 1 was used, in which 8-aminoquinoline was replaced with cycloheptylamine, to obtain white solid 0.18 g. $^1$H-NMR (400 MHz, DMSO-d$_6$) δ1.43-1.53 (m, 1H); δ1.87-1.90 (m, 2H); δ4.19 (s, 1H); δ6.51-6.55 (d, 1H); δ7.11-7.13 (dd, 1H); δ7.30-7.35 (t, 1H); δ7.42 (d, 1H); δ7.64-7.78 (m, 3H); δ8.20-8.22 (d, 1H); δ8.87-8.90 (d, 2H). MS (TOF) 453.0 (M+).

EXAMPLE 12

(2E)-3-(2-thienyl)-N-[1-(1-morpholinyl)thioformyl amino-2,2,2-trichloroethyl]-2-acrylamide

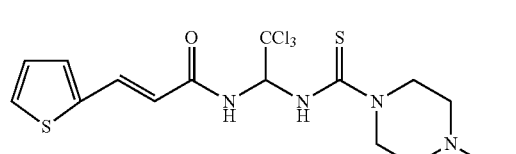

The method of Example 1 was used, in which 8-aminoquinoline was replaced with morpholine, to obtain white solid 0.15 g. $^1$H-NMR (400 MHz, DMSO-d$_6$) δ3.61-3.64 (m, 4H); δ3.83 (m, 4H); δ6.78-6.82 (d, 1H); δ7.40-7.45 (m, 3H); δ7.52-7.45 (m, 4H); δ7.89-7.91 (d, 1H); δ8.34-8.36 (d, 1H). MS (TOF) 421.9 (M+).

EXAMPLE 13

(2E)-3-(2-thienyl)-N-[1-(4-methylpiperazinyl)thioformylamino-2,2,2-trichloroethyl]-2-acrylamide The method of Example 1 was used, in which 8-aminoquinoline was replaced with N-methylpiperazine, to obtain white solid 0.17 g. $^1$H-NMR (400 MHz, DMSO-d$_6$) δ2.18 (s, 3H); δ2.31-2.40 (m, 4H); δ3.78-3.83 (m, 4H); δ6.76-6.80 (d, 1H); δ7.41-7.45 (m, 3H); δ7.52-7.60 (m, 2H); δ7.65-7.67 (m, 2H); δ7.83-7.85 (d, 1H); δ8.32-8.35 (d, 1H). MS (TOF) 435.3 (M+).

EXAMPLE 14

(2E)-3-(2-thienyl)-N-[1-(8-quinolylamino) methylthiomethenyl amino-2,2,2-trichloroethyl]-2-acrylamide

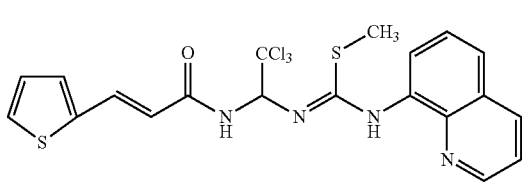

The method of Example 1 was used, (2E)-3-(2-thienyl)-N-[1-(8-quinolylamino)thioformylamino-2,2,2-trichloroethyl]-2-acrylamide 2.0 g of Example 1 was added to 5 ml of water to form a suspension, added with 0.5 ml of 50% NaOH aqueous solution, stirred for 10 min, added with 0.54 ml of iodomethane, reacted at room temperature for 2 h, extracted with ethyl ether, washed with saturated saline, dried with anhydrous magnesium sulfate, evaporated to remove solvent to obtain white solid (2E)-3-(2-thienyl)-N-[1-(8-quinolylamino) methylthiomethenylamino-2,2,2-trichloroethyl]-2-acrylamide 1.30 g. $^1$H-NMR (400 MHz, DMSO-$d_6$) δ2.79 (s, 3H); δ6.26-6.28 (d, 1H); δ6.86-6.90 (d, 1H); δ7.40-7.43 (m, 3H); δ7.53-7.64 (m, 6H); δ8.43-8.45 (dd, 1H); δ8.92-8.97 (m, 3H); δ9.59 (s, 1H). MS (TOF) 501.1 (M+).

EXAMPLE 15

(2E)-3-phenyl-[1-(1-morpholinylthioformylamino)-2,2,2-trichloro ethyl]-2-acrylamide

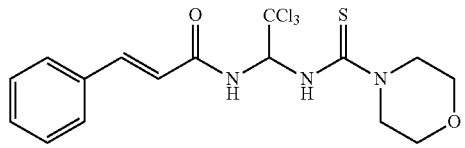

The method of Example 1 was used, in which 2-thiophene carboxaldehyde was replaced with benzaldehyde, 8-aminoquinoline was replaced with morpholine, to obtain white solid 0.19 g. $^1$H-NMR (400 MHz, DMSO-$d_6$) δ3.61-3.64 (m, 4H); δ3.79-3.83 (m, 4H); δ6.78-6.82 (d, 1H); δ7.41-7.46 (m, 3H); δ7.52-7.61 (m, 2H); δ7.64-7.67 (dd, 1H); δ7.89-7.91 (d, 1H); δ8.34-8.36 (d, 1H). MS (TOF) 422.7 (M+).

EXAMPLE 16

(2E)-3-phenyl-[1-(1-piperidylthioformylamino)-2,2,2-trichloro ethyl]-2-acrylamide

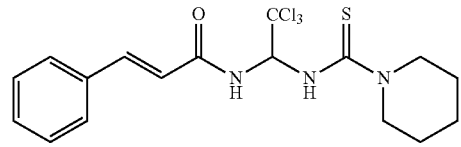

The method of Example 1 was used, in which 2-thiophene carboxaldehyde was replaced with benzaldehyde, 8-aminoquinoline was replaced with piperidine, to obtain white solid 0.15 g. $^1$H-NMR (400 MHz, DMSO-$d_6$) δ1.53-1.62 (m, 6H); δ3.81-3.82 (t4H); δ6.74-6.78 (d, 1H); δ7.41-7.46 (m, 3H); δ7.52-7.71 (m, 5H); δ8.36-8.38 (d, 1H); δ9.59 (s, 1H). MS (TOF) 420.7 (M+).

EXAMPLE 17

(2E)-3-phenyl-[1-(3-methoxybenzyl)thioformylamino-2,2,2-trichloroethyl]-2-acrylamide

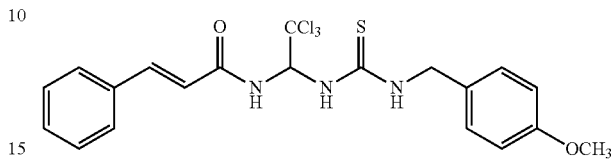

The method of Example 1 was used, in which 2-thiophene carboxaldehyde was replaced with benzaldehyde, 8-aminoquinoline was replaced with p-methoxybenzylamine, to obtain white solid 0.17 g. $^1$H-NMR (400 MHz, DMSO-$d_6$) δ3.72 (s, 3H); δ4.58-4.60 (d, 2H); δ6.77-6.81 (d, 1H); 6.90-6.92 (d, 2H); δ7.24-7.26 (d, 2H); δ7.36-7.46 (m, 4H); δ7.52-7.60 (m, 3H); δ7.96-7.98 (d, 1H); δ8.55 (t, 1H); δ8.97-8.99 (d, 1H). MS (TOF) 472.8 (M+).

EXAMPLE 18

Experiment on the Activity of the Compound for Protection of Cardiomyocyte

Primary Culture of Cardiomyocyte

The isolation and culture of cardiomyocytes were performed by referring to the differential adhesion method (Kreider, A. Messing, H. Doan, S. U. Kim, R. P. Lisak and D. E. Pleasure, Enrichment of Schwann cell cultures from neonatal rat sciatic nerve by differential adhesion, *Brain Res* 2 (1981), pp. 433-444). Wistar sucking mice newborn within 24 h were used, sterilized at skin of ventrum with iodine tincture and ethanol, subjected to thoracotomy using scissors at subxiphoid median line with a deviation to left, heart was taken out after slant thoracotomy and placed in PBS precooled with ice; the heart was softly blown and beaten with 0.01 M PBS to remove blood cells and other tissues, then cut into pieces with 0.5 $mm^3$ size, washed with 0.01 M PBS repeatedly for 2-3 times; the pieces were placed in conical flask, added with 4 ml of 0.125% pancretin, 1 ml of 0.1% collagenase II (final concentrations separately being 0.1% and 0.02%), shaken in 37° C. water bath for 10 min, the supernatant was discarded; then 4 ml of 0.125% pancretin and 1 ml of 0.1% collagenase II again, shaken in 37° C. water bath for digestion for 10 min, the supernatant was sucked and transferred to a centrifuge tube, and the supernatant was added with DMEM containing 10% FBS to terminate digestion; the step of shaking and digestion in water bath was repeated for 3-4 times, until the tissue pieces were completely digested; the collected cell suspension was centrifuged under 1000 rpm for 10 min, the supernatant was removed, then a culture medium was added for resuspension; the resuspended cells were inoculated in a cell culture flask, placed in CO2 incubator at 37° C. for incubation for 1.5 h, then the culture medium was sucked out, countered under microscope, then DMEM culture medium containing 10% FBS was used to adjust cell density, inoculated in an amount of $1\times10^4$ to a 96-well plate, placed in 5% CO2 incubator at 37° C. for 24 h, then half medium was replaced, a culture medium containing 0.1% Brdu was supplementally added; then the medium was replaced once per 48 h, and primary cardiomyocytes were obtained after 4 days of cultivation.

Measurement of Cell Inhibition Rate (MTT)

The isolated primary culture of cardiomyocytes was inoculated in an amount of $10^4$ cells per well to a 96-well plate, and the volume of each well was 100 µl (marginal wells were filled with sterile PBS). After being cultivated in 5% $CO_2$ and 37° C. incubator for 4 d, they were added with the compound of Formula I at different concentrations (0.3 µM, 1 µM, 3 µM, 10 µM, 30 µM, 100 µM), 3 double-wells were set for each concentration, at the same time, zero setting wells (culture medium, MTT, DMSO), and control wells (culture medium, DMSO) were also set. After continuous inoculation for 48 h, each well was added with 20 µl of MTT solution (5 mg/ml, formulated with PBS (pH=7.4), i.e., 0.5% MTT), and the cultivation was continued for 4 h. After the end of cultivation, culture medium in wells was carefully sucked out. Each well was added with 150 µl of DMSO, shaken at a low speed in a shaking table for 10 min, so that the crystal was sufficiently dissolved. The optical density (OD) value of each well was measured at wavelength of 550 nm by enzyme-linked immunoassay instrument, and each well was repeatedly measured for 5 times and the results were recorded. The results are shown in Table 1.

TABLE 1

Effects of the compound at different concentrations on survival rate of the cardiomyocytes as tested by the MTT method

| Group | Inhibition rate (%) of cardiomyocytes |
|---|---|
| Control group | 100 |
| Compound of Example 4 300 µM | 5.55 ± 2.29 |
| Compound of Example 5 300 µM | 0.76 ± 4.04 |
| Compound of Example 6 300 µM | 5.54 ± 3.61 |
| Compound of Example 7 300 µM | 1.32 ± 3.42 |
| Compound of Example 8 300 µM | 6.82 ± 1.21 |
| Compound of Example 9 300 µM | 5.30 ± 0.95 |
| Compound of Example 10 300 µM | 3.24 ± 1.70 |
| Compound of Example 11 300 µM | 7.62 ± 5.77 |
| Compound of Example 12 300 µM | 10.44 ± 5.66 |
| Compound of Example 13 300 µM | 1.66 ± 2.70 |
| Compound of Example 14 300 µM | 8.34 ± 5.78 |

The results show that: the compound of Examples at a concentration within 300 µM has no effect on survival rate of normal cardiomyocytes.

Assay of the Activity for Protection of Cardiomyocytes: Activity for Protecting Cardiomyocytes Apoptosis Induced by TG Cardiomyocytes were subjected to the primary culture for 4 days according to the above method, and then added with thapsigargin (TG) to induce apoptosis. The compound of the present invention was added for pretreatment 30 min before inducing apoptosis. The cells were randomly divided into 5 groups: (1) solvent control group (DMSO); (2) TG intervening group (0.4 uM); (3) TG (0.4 uM)+compound intervening group (0.3 uM); (4) TG (0.4 uM)+compound intervening group (1 uM); (5) TG (0.4 uM)+compound intervening group (3 uM). TG was formulated with DMSO, the mother liquid was of 4 mM; and the compound of the present invention was formulated with DMSO, and the mother liquid was of 150 mM. The cell survival rate was measured according to the above MTT method, so as to test the protection effects of the compound of the present invention on the TG-induced cardiomyocytes apoptosis, and the results are shown in Table 2.

TABLE 2

Effects of the compound at different concentrations on TG-induced cardiomyocytes apoptosis as tested by the MTT method

| Group | Survival rate (%) of Cardiomyocyte |
|---|---|
| Control group | 100 |
| TG intervening group | 59 ± 1.1 |
| Compound of Example 5 | |
| 0.3 µM group | 82 ± 4 |
| 1 µM group | 76 ± 8 |
| 3 µM group | 74 ± 9 |
| Compound of Example 6 | |
| 1 µM group | 76 ± 7 |
| 3 µM group | 70 ± 6 |
| 10 µM group | 78 ± 9 |
| Compound of Example 7 | |
| 1 µM group | 69 ± 5 |
| 3 µM group | 70 ± 8 |
| 10 µM group | 77 ± 11 |
| Compound of Example 12 | |
| 0.3 µM group | 79 ± 7 |
| 1 µM group | 80 ± 9 |
| 3 µM group | 83 ± 11 |
| Compound of Example 13 | |
| 0.3 µM group | 72 ± 3 |
| 1 µM group | 71 ± 3 |
| 3 µM group | 67 ± 3 |

Notation: cell survival rate=1−cell inhibition rate

Test results: in comparison with the group merely added with TG, when TG and the compounds of Examples were added together, the cardiomyocyte survival rate was significantly elevated, which indicates that the compounds of Examples in Table 2 could significantly improve TG-induced apoptosis and have protection effects on cardiomyocytes.

EXAMPLE 19

Protection Effects of Compounds of Formula I on Cardiomyocyte Apoptosis Induced by Anoxia Preparation of solution (the following reagents were purchased from Invitrogen Company)
1) 1× Wash Buffer: 20 mL of 10× Wash Buffer was added to 180 mL of ultrapure water, stored at 4° C. for 7 days.
2) fixing solution: 7.3 mL of 37% formaldehyde solution was added to 14.7 mL of 1× Wash Buffer, pre-heated before use to 37° C. This solution was prepared when using.
3) 1× penetrating membrane solution: 4 mL of 10× penetrating membrane solution was added to 36 mL of ultrapure water, this application solution was stored at 4° C. for 7 days.
4) Mitotracker/Hoechst solution (stored at −20° C.): Mitotracker CMXROS was dissolved with 94 µL of anhydrous DMSO to obtain 1 mM solution, this solution could be preserved at −20° C. under dry and dark condition for 6 months. In order to avoid multiple freeze-thaw cycles, it was subpackaged in an amount for single use. 5.5 µL of 1 mM Mitotracker Red Solution and 11 µL of Hoechst dye were added to cell culture medium, to obtain an application solution with a final volume of 5.5 mL. This application solution should be prepared when using.
5) Alexa Fluor 488 Phalloidin solution: Alexa Fluor 488 Phalloidin was dissolved with 140 µL of methanol to form a mother liquor, this solution could be preserved at −20° C.

under dry and dark condition for 12 months. 27.5 μL of the Alexa Fluor 488 Phalloidin mother liquor was added to 5.5 mL of 1× Wash Buffer to prepare an application solution. This application solution should be prepared when using.

Experimental Method:

Cardiomyocyte was obtained by primary culture according to Example 18, cell density $10^4$/mL, each wall was added with 100 μL of suspension of the cells. The cells were incubated at 37° C., 5% $CO_2$ environment for 96 h (replacing solution once per 48 h). After primary culture for 4 days, cell apoptosis was induced by placing in an anoxia incubator, the compounds of the present invention at different concentrations were added for pretreatment 30 min before inducing cell apoptosis, then placed in 37° C., 5% $CO_2$-95% $N_2$ incubator and cultured for 15.5 h. It was 30 min before the compound incubation finished, 50 μL of culture medium, 50 μL of Mitotracker/Hoechst solution, were added, and the cells were then continuously cultured at 37° C., 5% $CO_2$-95% $N_2$ for 30 min.

Each well was directly added with 100 μL of fixing solution, without sucking out the culture medium, incubated at room temperature in fume cupboard for 10 min. The preheated fixing solution was very important for keeping cell integrity.

The solution of each well was sucked out (the plate could be turned over), washed with 1× Wash Buffer (100 μL/well) once. Carefulness was kept during operation and washing procedure to maintain cell adhesion and integrity. Good results could be obtained by slowly sucking and releasing liquid. Wash Buffer was sucked out, 1× penetrating membrane solution (100 uL/well) was added, incubated at room temperature for 15 min. The penetrating membrane solution was sucked out, each well was washed once with 100 μL/well of 1× Wash Buffer. The Wash Buffer was sucked out, each well was added with 50 μL of Alexa Fluor 488 Phalloidin Solution, incubated at room temperature in dark for 30 min. The Alexa Fluor 488 Phalloidin solution was sucked out, washed with 1× Wash Buffer for three times, and the solution of the last time was kept in the well. The edge of plate was covered with sealing membrane (for prevention of drying), and assayed with HCS Reader. The plate was preserved at 4° C. environment temperature. The extent of cardiomyocyte apoptosis was finally detected by fluorescence staining method. The results are shown in Table 3, Table 4 and Table 5.

This analysis method is a high connotation screening analytical method. It is a method for detecting apoptosis newly developed in recent years, which uses specific fluorescence staining to perform multiplicity of apoptosis. Three parameters relevant to apoptosis process were mainly analyzed, including karyomorphology change, mitochondrial swelling and/or mitochondrial transmembrane potential, F-actin content. HCS Reader can observe morphology of nucleus by Hoechst staining, and can compare quantitatively nucleus area and nucleus strength. The decrease in mitochondrial transmembrane potential and the increase of mitochondrial volume are generally accepted as early markers of apoptosis, and can be quantitated by mitochondrial tracer MitoTracker® Red.

TABLE 3

Test results of nucleus area

| Group | Nucleus area (%) |
|---|---|
| Control group | 113.86 ± 3.06 |
| Anoxia group | 98.26 ± 1.00 |
| Compound of Example 1 10 μM group | 112.61 ± 7.78 |

TABLE 3-continued

Test results of nucleus area

| Group | Nucleus area (%) |
|---|---|
| Compound of Example 5 0.3 μM group | 120.23 ± 5.49 |
| Compound of Example 6 1 μM group | 100.00 ± 4.63 |
| Compound of Example 12 10 μM group | 102.93 ± 5.12 |

TABLE 4

Test results of mitochondrial transmembrane potential

| Group | Mitochondrial transmembrane potential |
|---|---|
| Control group | 100 ± 1 |
| Anoxia group | 96.04 ± 3.61 |
| Compound of Example 1 10 μM group | 112.68 ± 1.46 |
| Compound of Example 5 0.3 μM group | 117.76 ± 1.87 |
| Compound of Example 6 1 μM group | 112.92 ± 0.82 |
| Compound of Example 12 10 μM group | 133.11 ± 6.30 |
| Compound of Example 13 3 μM group | 116.41 ± 0.64 |

TABLE 5

Test results of light flux

| Group | light flux |
|---|---|
| Control group | 1247.52 ± 48.059 |
| Anoxia group | 1044.91 ± 16.53 |
| Compound of Example 1 10 μM group | 1201.92 ± 29.95 |
| Compound of Example 5 0.3 μM group | 1331.12 ± 53.30 |
| Compound of Example 6 1 μM group | 1077.08 ± 55.63 |

Test results: in comparison with the Anoxia group, after the compounds of the Examples were added, the nucleus area, mitochondrial transmembrane potential and light flux of cardiac muscle cells increased significantly, indicating the compounds of the Examples had significant effects of improving apoptosis induced by anoxia, and could protect cardiac muscle cells.

Although the embodiments for carrying out the invention have been described in details, those skilled in the art would understand that according to the disclosed teachings, these details could be subjected to various modifications and replacements, and all of these alternations are covered by the protection scope of the present invention. The protection scope of the present invention is determined by the attached claims and any equivalents thereof.

What is claimed is:

1. A compound of Formula I, or a pharmaceutically acceptable salt and solvate thereof,

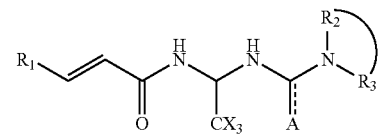

I wherein:

A represents =S or —SR4;

X represents F, Cl, Br or I;

R1 represents thienyl or substituted thienyl, wherein said substituted thienyl is substituted with 1-3 substituents selected from halogens, nitro, hydroxyl, amino, cyano, C1-C6 alkyl, C1-C6 alkoxy, and C1-C6 halogenated alkyl, and wherein said alkyl, alkoxy and halogenated alkyl is optionally substituted with hydroxy, —O—(C1-C4)-alkyl, oxo, amino, —NH—(C1-C4)-alkyl, or —N—[(C1-C6)-alkyl]2, or said alkyl, alkoxy and halogenated alkyl is optionally substituted with —O—, —S—, —NH—, —COO—;

R2, R3 each individually represent hydrogen, C1-C6 alkyl, C3-C6 cycloalkyl, substituted C3-C6 cycloalkyl, C1-C6 alkoxy, amino C1-C6 alkyl, mono-substituted or di-substituted amino C1-C6 alkyl, phenyl C1-C6 alkyl, substituted phenyl C1-C6 alkyl, phenyl, substituted phenyl, wherein R2 and R3 may be attached together to form a saturated cyclic alkyl, nitrogen- or oxygen-containing heterocyclic group; and R4 represents C1-C6 alkyl.

2. A compound of Formula I, or a pharmaceutically acceptable salt and solvate thereof,

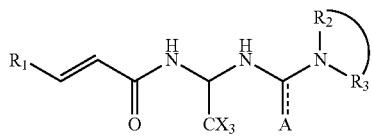

wherein

A represents =S or —SR4;

X represents F, Cl, Br or I;

R1 represents thienyl or substituted thienyl;

R2, R3 each individually represent hydrogen, C1-C6 alkyl, C3-C6 cycloalkyl, substituted C3-C6 cycloalkyl, C1-C6 alkoxy, amino C1-C6 alkyl, mono-substituted or di-substituted amino C1-C6 alkyl, phenyl C1-C6 alkyl, substituted phenyl C1-C6 alkyl, phenyl, substituted phenyl, wherein R2 and R3 may be attached together to form a saturated cyclic alkyl, nitrogen- or oxygen-containing heterocyclic group; and R4 represents methyl, ethyl, propyl, isopropyl, butyl, or pentyl.

3. A compound of Formula I, or a pharmaceutically acceptable salt and solvate thereof,

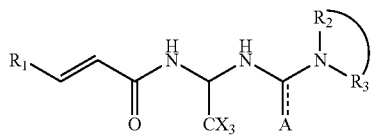

wherein:

A represents =S or —SR4;

X represents Cl;

R1 represents 2-thienyl or 3-thienyl;

R2, R3 each individually represent hydrogen, methyl, isopropyl, 2-methoxy ethyl, 3-isopropoxy propyl, 2-N,N-dimethyl ethyl, cyclohexyl, cycloheptyl, o-methoxy phenyl, o-fluorophenyl, o-chlorophenyl, p-chlorophenyl, benzyl or 8-quinolyl, wherein R2 and R3 may be attached together to form a piperidine ring, morpholine ring, or N-methyl piperazine ring; and R4 represents methyl or ethyl.

4. The compound according to claim 1 having any one of the following structures, or their pharmaceutically acceptable salts and solvates:

(1) (2E)-3-(2-thienyl)-N-[1-(8-quinolylamino)thioformylamino- 2,2,2-trichloroethyl ]-2-acrylamide;

(2) (2E)-3-(3-thienyl)-N-[1-(8-quinolylamino)thioformylamino- 2,2,2-trichloroethyl ]-2-acrylamide;

(3) (2E)-3-(2-thienyl)-N-[1-(4-tolylamino)thioformylamino- 2,2,2-trichloroethyl ]-2-acrylamide;

(4) (2E)-3-(2-thienyl)-N-[1-(2-methoxyanilino)thioformylamino- 2,2,2-trichloroethyl ]-2-acrylamide;

(5) (2E)-3-(2-thienyl)-N-(1 -benzylaminothioformylamino- 2,2,2-trichloroethyl)-2-acrylamide;

(6) (2E)-3 -(2-thienyl)-N-(1 -cyclohexylaminothioformylamino- 2,2,2-trichloroethyl)-2-acrylamide;

(7) (2E)-3-(2-thienyl)-N-[1 -isopropylaminothioformylamino-2,2,2-trichloroethyl ]-2-acrylamide;

(8) (2E)-3-(2-thienyl)-N-[1-(2-fluoroanilino)thioformylamino- 2,2,2-trichloroethyl ]-2-acrylamide;

(9) (2E)-3 -(2-thienyl)-N-[1-(3 -isopropoxypropylamino) thioformylamino-2,2,2-trichloroethyl ]-2-acrylamide;

(10) (2E)-3-(2-thienyl)-N-[1-(2-methoxyformylanilino) thioformylamino-2,2,2-trichloroethyl ]-2-acrylamide;

(11) (2E)-3-(2-thienyl)-N-(1-cycloheptylaminothioformylamino- 2,2,2-trichloroethyl)-2-acrylamide;

(12) (2E)-3-(2-thienyl)-N-[1-(1-morpholinyl)thioformylamino- 2,2,2-trichloroethyl ]-2-acrylamide;

(13) (2E)-3-(2-thienyl)-N-[1-(4-methylpiperazinyl) thioformylamino-2,2,2-trichloroethyl ]-2-acrylamide; or

(14) (2E)-3-(2-thienyl)-N-[1-(8-quinolylamino) methylthiomethenylamino-2,2,2-trichloroethyl ]-2-acrylamide.

5. A pharmaceutical composition comprising a compound or a pharmaceutically acceptable salt and solvate thereof according to claim 1, and a pharmaceutically acceptable carrier, excipient or diluent.

6. A pharmaceutical composition comprising a compound or a pharmaceutically acceptable salt and solvate thereof according to claim 2, and a pharmaceutically acceptable carrier, excipient or diluent.

7. A pharmaceutical composition comprising a compound or a pharmaceutically acceptable salt and solvate thereof according to claim 3, and a pharmaceutically acceptable carrier, excipient or diluent.

8. A pharmaceutical composition comprising a compound or a pharmaceutically acceptable salt and solvate thereof according to claim 4, and a pharmaceutically acceptable carrier, excipient or diluent.

9. A compound, or a pharmaceutically acceptable salt and solvate thereof, having any one of the following structures:

(15) (2E)-3-phenyl-[1-(1-morpholinyl)thioformylamino-2,2,2-trichloroethyl ]-2-acrylamide;

(16) (2E)-3-phenyl-[1-(1-piperidyl)thioformylamino- 2,2,2-trichloroethyl ]-2-acrylamide; or

(17) (2E)-3-phenyl -[1-(3-methoxybenzyl)thioformylamino- 2,2,2-trichloroethyl ]-2-acrylamide.

* * * * *

UNITED STATES PATENT AND TRADEMARK OFFICE
CERTIFICATE OF CORRECTION

| | | |
|---|---|---|
| PATENT NO. | : 9,199,978 B2 | Page 1 of 1 |
| APPLICATION NO. | : 13/697810 | |
| DATED | : December 1, 2015 | |
| INVENTOR(S) | : Kunlun He et al. | |

It is certified that error appears in the above-identified patent and that said Letters Patent is hereby corrected as shown below:

On the Title Page item 75, Inventors, replace "Kunluu" with -- Kunlun --

IN THE CLAIMS:

Column 19, line 8, please delete "-N-[(C1-C6)-alkyl]2" before "or" and replace with
-- "-N-[(C1-C6)-alkyl]$_2$ --

Signed and Sealed this
Tenth Day of May, 2016

Michelle K. Lee
*Director of the United States Patent and Trademark Office*